US00PP23158P2

(12) United States Plant Patent
Orard

(10) Patent No.: US PP23,158 P2
(45) Date of Patent: Nov. 6, 2012

(54) CLIMBING ROSE PLANT NAMED 'ORAFANTANOV'

(50) Latin Name: *Rosa hybrida*
Varietal Denomination: ORAfantanov

(75) Inventor: Pierre Orard, Feyzin (FR)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 13/199,403

(22) Filed: Aug. 29, 2011

(51) Int. Cl.
*A01H 5/00* (2006.01)

(52) U.S. Cl. ..... Plt./109

(58) Field of Classification Search ..... Plt./102, Plt./107, 109, 114, 130, 138, 141, 149
See application file for complete search history.

*Primary Examiner* — Howard Locker
(74) *Attorney, Agent, or Firm* — McKee, Voorhees & Sease, P.L.C.

(57) ABSTRACT

A new variety of Climbing rose suitable for garden decoration, having flowers of smoky purple magenta blend coloration.

1 Drawing Sheet

Classification: The present invention relates to a new *Rosa hybrida* plant.

Variety denomination: The new plant has the varietal denomination 'ORAfantanov'.

BACKGROUND OF THE INVENTION

This invention relates to a new and distinct variety of Climbing Rose. It has as its seed parent the variety known as 'ORApaymel' (U.S. Plant Pat. No. 14,500) and as its pollen parent the variety known as 'FRAntasia' (U.S. Plant Pat. No. 17,518).

SUMMARY OF THE INVENTION

Among the features which distinguish the new variety from other presently available and commercial rose cultivars known to the inventor are the following combinations of characteristics: its very unique smoky purple magenta blend flower coloration, its large clusters with multiple flowers, its many stipitate glands on the peduncle and on the surface of the bud and its several small prickles on the branches and new shoots. The plant has a spreading climbing growth habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'ORAfantanov' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'ORApaymel' by the following combination of characteristics: whereas 'ORAfantanov' bears semi-double flowers (about 13 to 16 petals) of smoky purple magenta blend coloration, 'ORApaymel' bears flowers of white edged red coloration with significantly heavier petalage (about 18 to 22 petals). The new variety is classified as a climbing rose with a spreading climbing growth habit with canes about 300 cm. to about 350 cm. in length, whereas the seed parent is classified as a shrub rose with a significantly shorter bushy to somewhat spreading and rounded growing habit (about 108 to about 125 cm. in height).

The new variety may be distinguished from its pollen parent, 'FRAntasia' by the following combination of characteristics: whereas 'ORAfantanov' bears flowers of smoky purple magenta blend coloration, 'FRAntasia' bears flowers of purple-blue coloration. The new variety is classified as a climbing rose with a spreading climbing growth habit with canes about 300 cm. to about 350 cm. in length, whereas the pollen parent is classified as a shrub rose with a significantly shorter and less spreading very upright growing habit (about 175 to about 210 cm. in height and about 0.7 to about 0.88 cm. spread at the widest point).

COMPARISON WITH THE CLOSEST COMMERCIALLY AVAILABLE CULTIVAR

The closest commercially available cultivar to the new variety is the pollen parent 'FRAntasia'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of July. Phenotypic expression may vary with environmental, cultural and climatic conditions, as well as differences in conditions of light and soil.

FLOWER

The new variety usually bears its flowers in clusters of three to twenty four or more per stem. Flowers are borne in regular rounded clusters on strong medium to long stems (about 23 to about 92 cm.). Outdoors, the plant blooms abundantly and nearly continuously during the growing season. The flowers have a strong clove to spicy fragrance.

BUD

The peduncle is about 2.2 to about 4.5 cm. in length, of average caliper (about 0.2 to about 0.25 cm. in diameter), and usually erect. It is moderately rough, with many stipitate glands. Peduncle color is between 146C and 146D.

Before the calyx breaks, the bud is about 0.9 to about 1.5 cm. in diameter at the widest point, about 1.4 to about 2.0 cm. in length, and pointed in shape. The surface of the bud bears between 2 to 5 foliaceous appendages and many stipitate glands, usually with slender entire foliaceous parts extending beyond the tip of the bud about ¼ or more of its length. Bud color is between 137C and 137B sometimes lightly suffused, especially on the side exposed to the sun, with between 187B and 187A.

The sepals are about 2.4 to about 3.5 cm. in length and about 0.7 to about 0.9 cm. in width at the widest point. The outer surface color of the sepal is between 137C and 137B sometimes lightly suffused, especially on the side exposed to the sun, with between 187B and 187A. The inner surface color of the sepal is near 146D broadly bordered by near 137A. After the sepals open, the inner surface color is often moderately suffused, especially on the area exposed to the sun, with between 187A and 187B. The inner surface of the sepal is covered with fine wooly tomentum; sepal margins are lined with some stipitate glands and hairs.

The receptacle of the flower is of medium length (about 0.4 to about 0.6 cm.) and average in caliper (about 0.4 to about 0.6 cm. in diameter). The receptacle is moderately rounded to urn-shaped in form. Its surface is moderately smooth with some hairs and stipitate glands and with somewhat thin fleshy walls. The receptacle color is between 144A and 146B.

As the petals open (after the calyx breaks), the bud is about 1.3 to about 2.1 cm. in diameter at the widest point, about 1.6 to about 2.5 cm. in length, and moderately ovoid to somewhat pointed in form. The color of the under surfaces of the newly opened petals is between 60B and 60A sometimes moderately blushed with between 187A and 187B. At the point where the petal attaches, there is a moderately large zone of between 10B and 11B. The color at the base of the upper surfaces of the newly opened petals is between 187C and 60B gradually suffusing toward the petal edge with near 187A. At the point where the petal attaches, there is a somewhat large zone of between 12A and 9A.

BLOOM

When fully open, the bloom ranges from about 6.6 to about 9.6 cm. in diameter. Petalage is semi-double with about 13 to 16 petals and about 0 to 5 petaloids irregularly arranged. When partially open, the bloom form is moderately cupped to somewhat ovoid, and the petals are loosely spiraled to somewhat cupped with petal edges somewhat reflexed outward. When fully open, the bloom form is more cupped, and the petals are loosely cupped to undulated with petal edges somewhat reflexed outward and sometimes moderately reflexed inward.

PETALS

The substance of the petals is moderately heavy and of medium to thick thickness, with upper surfaces moderately satiny and under surfaces matte. The petals are about 2.9 to about 4.1 cm. in length and about 2.4 to about 4.0 cm. in width at the widest point. Petal margins are entire.

The outer petals are moderately obovate to somewhat ovate in shape with rounded apices.

The inner petals are broadly obovate to somewhat ovate in shape with rounded apices.

Petaloids are about 1.1 to about 1.9 cm. in length and about 0.5 to about 0.8 cm. in width at the widest point. Petaloids are irregularly shaped moderately subulate to somewhat obovate with rounded apices.

NEWLY OPENED FLOWER

The color at the base of the under surfaces of the outer, intermediate and inner petals is near 69B gradually suffusing toward the petal edge with between 64B and 71B sometimes moderately blushed with between 187B and 74A to as dark as near 79A. At the point where the petal attaches, there is a large zone of between 6D and 5D. The color at the base of the upper surfaces of the outer, intermediate and inner petals is between 64B and 67B gradually suffusing toward the petal edge with between 71A and 72A sometimes edged with between 74A and 71C. At the point where the petal attaches, there is a somewhat large zone of between 8A and 7C.

The under and upper surface colors of the petaloids are similar in coloration to the upper and under surfaces of the intermediate and inner petals.

The general tonality of the newly opened flower is between 64B and 67B at the base gradually suffusing toward the petal edge with between 71A and 72A sometimes edged with between 74A and 71C.

THREE-DAY-OLD FLOWER

The color at the base of the under surfaces of the outer, intermediate and inner petals is between 75D and 76B gradually suffusing toward the petal edge with between 78B and 72B sometimes moderately blushed with between 72A and 74A to as dark as near 79B. At the point where the petal attaches, there is a large zone of near 5D. The color at the base of the upper surfaces of the outer, intermediate and inner petals is between 80B and 67B gradually suffusing toward the petal edge with between 79B and 77A sometimes blushed with between 79A and 71C. At the point where the petal attaches, there is a somewhat large zone of near 8B.

The under and upper surface colors of the petaloids are similar in coloration to the upper and under surfaces of the intermediate and inner petals.

The general tonality of the three-day-old flower is between 80B and 67B at the base gradually suffusing toward the petal edge with between 79B and 77A sometimes blushed with between 79A and 71C.

On the spent bloom, the petals usually drop off cleanly.

In July in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 80) and are arranged regularly about the pistils; a few are mixed with petaloids. The filaments are of medium length (about 0.6 to about 1.2 cm.) most with anthers. Filaments are between 13B and 14B in color. The anthers are moderately small for the class and all open approximately at the same time. Anther color when immature is near 22A on the external part and near 19C on the internal part. Anther color at maturity is near 165B on the external part and near 200B on the internal part. Pollen is abundant and between 19A and 20B in color.

FEMALE REPRODUCTIVE ORGANS

Pistils vary in number (average about 45). The styles are moderately uneven, average to somewhat long in length (about 0.6 to about 1.0 cm.), moderately heavy in caliper, and loosely bunched. Stigma color is between 3C and 4C. Style color is between 11D and 8D often moderately suffused with between 53B and 60B. Ovaries are usually all enclosed in the calyx.

Hips are of somewhat short to average length (about 1.0 to about 1.5 cm.), rounded in form, and between 28A and 30B in color when ripe. The hip surface is smooth with few hairs and with moderately thick fleshy walls. The sepals are somewhat permanent, and usually straight in shape.

The seeds are irregularly rounded, smooth in texture, approximately 3 to about 12 per hip, about 0.5 to about 0.8 cm. in diameter at the widest point and between 161C and 162C in color.

FOLIAGE

The compound leaves are usually comprised of three to seven leaflets and are borne abundantly. The seven-leaflet leaves are about 13.3 to about 17.9 cm. in length and about 7.9 to about 13.2 cm. in width at the widest point, moderately crisp to somewhat leathery in texture, and semi-glossy in finish on the upper side and matte in finish on the under side. The terminal leaflets are about 4.2 to about 7.6 cm. in length and about 3.3 to about 4.6 cm. in width at the widest point, shaped moderately ovate to somewhat oval with acute apices and rounded bases. Their margins are simply serrate.

The upper surface color of the mature leaf is between 137A and 139A. The under surface color of the mature leaf is between 147B and 148C. The upper surface color of the young leaf is between 146B and 146A, sometimes moderately suffused with between 187A and 187B. The under surface color of the young leaf is between 138B and 146C, often heavily suffused with between 187B and 187C.

The rachis is moderately heavy in caliper and rough. The upper side is deeply grooved with some hairs and stipitate glands on the edges of the grooves. The under side of the rachis is rough with some hairs and stipitate glands and few small prickles. The rachis color is near 146D on the under side and near 137B on the upper side often moderately suffused on the young leaves with between 183A and 187B.

The stipules are about 2.1 to about 3.2 cm. in length and moderately wide (about 0.6 to about 0.7 cm.) with long straight points that usually turn out at an angle of more than 45 degrees and sometimes recurve toward the stem. The under and upper surface color of the stipule is between 137B and 137A sometimes lightly suffused with between 187C and 183B.

The petiole is moderately heavy in caliper and rough. The upper side is deeply grooved with some hairs and stipitate glands on the edges of the grooves. The under side of the petiole is rough with some hairs and stipitate glands and few small prickles. The petiole is about 1.3 to about 1.9 cm. in length and about 0.15 to about 0.2 cm in width at the widest point. The petiole color is near 146D on the under side and near 137B on the upper side often moderately suffused on the young leaves with between 183A and 187B.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a spreading climbing growth habit with canes about 300 cm. to about 350 cm. in length with full branching. It displays vigorous growth and the canes are of moderately heavy caliper for the class (about 0.9 to about 1.7 cm. in width at the widest point).

The color of the major stems is between 152A and 152B. They bear few large prickles that are about 0.5 to about 0.9 cm. in length. The large prickles are angled slightly downward with a moderately short narrow oval base; prickle color is between 165C and 164B. The major stem bears many small prickles of similar shape and coloration.

The color of the branches is between 146C and 146B. They bear few large prickles which are of similar size and shape to the large prickles on the major stems; prickle color is between 161B and 162B often lightly suffused with between 187C and 187D. The branches bear several small prickles of similar shape and coloration.

The color of the new shoots is between 146C and 146D sometimes lightly suffused with between 187B and 187C. They bear few large prickles which are of similar size and shape to the large prickles on the major stems; prickle color is near 153C often moderately suffused with 187B and 187C. The shoots bear several small prickles of similar shape and coloration.

I claim:

1. A new and distinct Climbing rose plant of the variety substantially as described and illustrated herein.

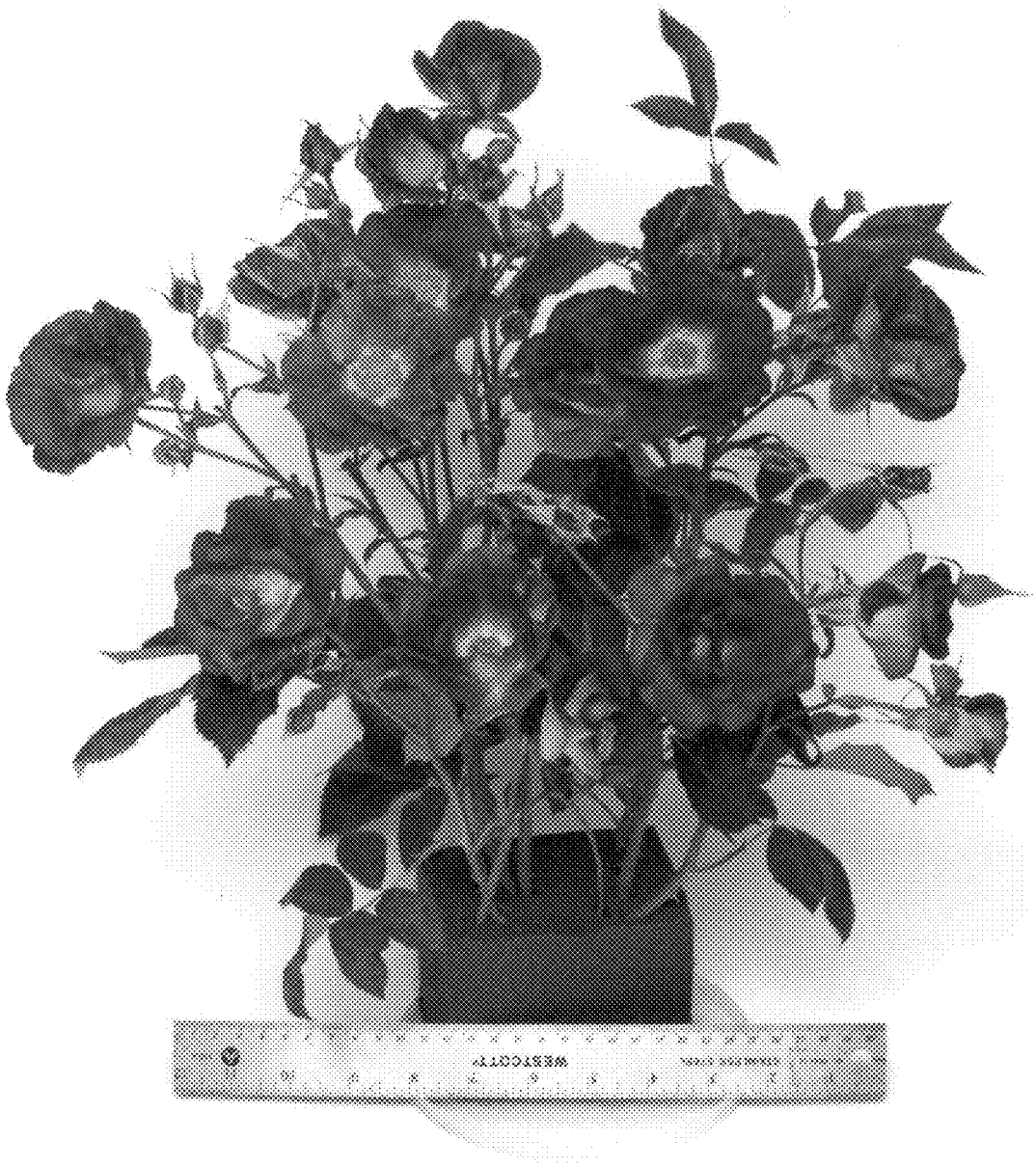

* * * * *